(12) United States Patent
Baron et al.

(10) Patent No.: US 6,407,238 B1
(45) Date of Patent: Jun. 18, 2002

(54) PROCESS OF MAKING SUBSTITUTED PYRAZOLES

(75) Inventors: James A. Baron, Hilliard, OH (US); Vittorio Farina, Wilton; Nizar Haddad, Danbury, both of CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 09/698,442

(22) Filed: Oct. 27, 2000

Related U.S. Application Data

(60) Provisional application No. 60/192,651, filed on Mar. 28, 2000, and provisional application No. 60/162,476, filed on Oct. 29, 1999.

(51) Int. Cl.[7] ................. C07D 403/04; C07D 401/04; C07D 231/38; C07D 231/12
(52) U.S. Cl. ................. 544/333; 544/405; 546/144; 546/167; 546/275.4; 548/364.1; 548/371.4; 548/376.1; 548/373.1; 548/377.1
(58) Field of Search .................... 548/364.1, 371.4, 548/373.1, 377.1, 376.1; 544/333, 405; 546/275.4, 144, 167

(56) References Cited

U.S. PATENT DOCUMENTS 5,162,360 A * 11/1992 Creswell et al. ............ 514/371
5,616,723 A    4/1997 Muhr et al.
5,969,153 A * 10/1999 Hamper et al. .......... 548/377.1

FOREIGN PATENT DOCUMENTS

| WO | WO-98/52558 | * 11/1998 |
| WO | WO 99/23901 | 4/1999 |
| WO | PCT US/00/29891 | 10/2000 |

OTHER PUBLICATIONS

Hartwig Angew. Chem. Int. Ed. 37 (1998) 2090–2093.*
Wagaw et al J. Org. Chem. (1996) 7240–7241.*
Wagaw et al J. Am. Chem. Soc. 121 (1999) 10251–10263.*
X. Jung Lee, et a l; Synthesis of Pyrazolo–fused Hetercyles by a Tandem Appel's Dehydration/Electrocylization Methodolgy, J. Heterocyclic Chem. 34, (1997) 1795–1799.
S. Wagaw, et al; A Palladium–Catalyzed Strategy for the Preparation of Indoles: A Novel Entry into the Fischer Indole Synthesis, J. Am. Chem. Soc. 1998, 120, 6621–6622.

* cited by examiner

*Primary Examiner*—Mukund J. Shah
*Assistant Examiner*—Thomas McKenzie
(74) *Attorney, Agent, or Firm*—Robert P. Raymond; Anthony P. Bottino; Alan R. Stempel

(57) ABSTRACT

Disclosed is a process of making substituted pyrazoles from substituted benzophenone hydrazones with a variety of 1,3-bifunctional substrates under acid conditions. The pyrazole compounds are useful for making pharmaceutical compounds.

4 Claims, No Drawings

PROCESS OF MAKING SUBSTITUTED PYRAZOLES

RELATED APPLICATION DATA

This application claims benefit to U.S. provisional application Nos. 60/192,651 filed Mar. 28, 2000 and 60/162,476 filed Oct. 29, 1999.

FIELD OF INVENTION

The present invention relates to novel synthesis of substituted aryl and heteroaryl pyrazole compounds of the formula (I) described herein.

BACKGROUND

The aryl and heteroaryl pyrazole structure is found in a large number and variety of compounds that possess important biological activities and pharmacological properties. Makino, K. et al. *J. Heterocyclic Chem.* 1998, 35, 489; Elguero, *J. Compr. Heterocycl. Chem.* II 1996, 3, 1. For example, WO 98/52558 and WO 99/23091 disclose heteroaryl urea compounds which are indicated to be useful in treating cytokine mediated diseases. U.S. Pat. No. 5,162,360 discloses N-substituted aryl-N'-heterocyclic substituted urea compounds which are described as being useful for treating hypercholesterolemia and atheroclerosis.

The synthesis of this important family of compounds is well reviewed. See Makino, K. et al. supra, Takagi, K. et al. *J. Heterocyclic Chem.* 1996, 33, 1003; El-Rayyes, N. R. et al. *Synthesis* 1985, 1028; Sammes, M. P. et al. *Advances in Heterocyclic Chemistry*, Vol 34, Academic Press, 1983; Behr, L. C. et al. *The Chemistry of Heterocyclic Compounds*, Weissberger, A., ed., Interscience Publishers, John Wiley and Sons, 1967. The conventional approach for pyrazole synthesis is the condensation of an aryl hydrazine with 1,3-diketones or their equivalents, such as β-ketoesters, β-cyanoketones and others. However, aryl hydrazines have not been widely available by convenient, scalable chemistry. Buchwald and Hartwig have recently described a general and practical synthesis of N-arylated benzophenone hydrazones. Buchwald, S. L. et al. *J. Am. Chem. Soc.* 1998, 120, 6621; Hartwig, J. F. *Angew. Chem., Int. Ed.* 1998, 37, 2090.

Unfortunately, their hydrolysis to N-aryl hydrazines has not been demonstrated. There is therefore a clear need for a synthesis of substituted pyrazoles which overcomes limitations of well known syntheses.

SUMMARY OF THE INVENTION

The present invention addresses the need in the art for a versatile new synthesis of substituted pyrazoles of the formula (I):

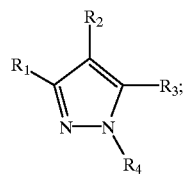
(I)

wherein $R_1$, $R_2$, $R_3$ and $R_4$ are defined herein below, by providing for the first time a process of making a variety of pyrazoles from substituted benzophenone hydrazones with different 1,3-bifunctional groups.

DETAILED DESCRIPTION OF PREFERRED EMBODIMENTS

In the present invention, it was postulated that upon treatment of such hydrazones with dicarbonyl compounds or related functionalities apparent to the skilled artisan, a transhydrazonation reaction would take place[3a], leading eventually to pyrazole compounds of the formula (I). Such a synthesis will benefit from the demonstrated palladium catalyzed cross couplings of benzophenone hydrazone to various aryl halides and overcomes limitations associated with the availability of aryl and heteroaryl hydrazines.[4] The novel process of the invention also provides product compounds with a desirable high regio specificity as shown in schemes 1–4 below.

In one embodiment of the invention there is provided the process of making a pyrazole compound of the formula (I):

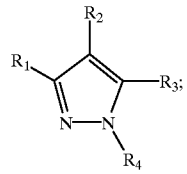
(I)

wherein $R_1$, $R_2$, $R_3$ and $R_4$ are defined as follows:
  each $R_1$ and $R_3$ are independently chosen from:
    amino and $C_{1-10}$ alkyl optionally partially or fully halogenated and optionally substituted with one to three $C_{3-10}$ cycloalkanyl, $C_{1-6}$alkoxy, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl; each of the aforementioned being optionally substituted with one to five groups chosen from halogen, $C_{1-6}$ alkyl which is optionally partially or fully halogenated, $C_{3-8}$ cycloalkanyl, $C_{5-8}$ cycloalkenyl and $C_{1-3}$ alkoxy which is optionally partially or fully halogenated; wherein both $R_1$ and $R_3$ cannot simultaneously be amino;
  $R_2$ is chosen from:
    hydrogen, $C_{1-6}$ branched or unbranched alkyl optionally partially or fully halogenated and aryl optionally partially or fully halogenated;
  $R_4$ is chosen from:
    phenyl, naphthyl, morpholinyl, pyridinyl, pyrimidinyl, pyrazinyl, pyridazinyl, pyrrolyl, pyrrolidinyl, imidazolyl, pyrazolyl, thiazolyl, oxazoyl, triazolyl, tetrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl and indazolyl, each of the aforementioned is optionally substituted with one to three phenyl, naphthyl, heterocycle or heteroaryl as hereinabove described in this paragraph, $C_{1-6}$ branched or unbranched alkyl which is optionally partially or fully halogenated, cyclopropanyl, cyclobutanyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halogen, hydroxy, oxo, nitrile, $C_{1-3}$ alkoxy optionally partially or fully halogenated, phenyloxy, naphthyloxy, heteroaryloxy or heterocyclicoxy wherein the heterocyclic or heteroaryl moiety is as hereinabove described in this paragraph, nitro, phenylamino, naphthylamino, heteroaryl or heterocyclic amino wherein the heteroaryl or heterocyclic moiety is as hereinabove described in this paragraph, $NH_2C(O)$, a mono- or di-($C_{1-3}$alkyl) aminocarbonyl, $C_{1-5}$ alkyl—C(O)—$C_{1-4}$ alkyl, amino-$C_{1-5}$ alkyl, mono- or di-($C_{1-3}$ alkyl) amino-$C_{1-5}$ alkyl, amino-$S(O)_2$, di-($C_{1-3}$ alkyl)amino-$S(O)_2$, $R_7$—$C_{1-5}$alkyl, $R_8$—$C_{1-5}$ alkoxy, $R_9$—C(O)—$C_{1-5}$ alkyl, $R_{10}$—$C_{1-5}$ alkyl $(R_{11})N$ or carboxy-mono-or di-($C_{1-5}$ alkyl)-amino;

a fused aryl chosen from benzocyclobutanyl, indanyl, indenyl, dihydronaphthyl, tetrahydronaphthyl, benzocycloheptanyl and benzocycloheptenyl, or a fused heteroaryl chosen from cyclopentenopyridinyl, cyclohexanopyridinyl, cyclopentanopyrimidinyl, cyclohexanopyrimidinyl, cyclopentanopyrazinyl, cyclohexanopyrazinyl, cyclopentanopyridazinyl, cyclohexanopyridazinyl, cyclopentanoquinolinyl, cyclohexanoquinolinyl, cyclopentanoisoquinolinyl, cyclohexanoisoquinolinyl, cyclopentanoindolyl, cyclohexanoindolyl, cyclopentanobenzimidazolyl, cyclohexanobenzimidazolyl, cyclopentanobenzoxazolyl, cyclohexanobenzoxazolyl, cyclopentanoimidazolyl, cyclohexanoimidazolyl, cyclopentanothienyl and cyclohexanothienyl; wherein the fused aryl or fused heteroaryl ring is independently substituted with zero to three phenyl, naphthyl, pyridinyl, pyrimidinyl, pyrazinyl, pyridazinyl, pyrrolyl, imidazolyl, pyrazolyl, thienyl, furyl, isoxazolyl, isothiazolyl, $C_{1-6}$ alkyl which is optionally partially or fully halogenated, halogen, nitrile, $C_{1-3}$ alkoxy which is optionally partially or fully halogenated, phenyloxy, naphthyloxy, heteroaryloxy or heterocyclicoxy wherein the heteroaryl or heterocyclic moiety is as hereinabove described in this paragraph, nitro, mono- or di-($C_{1-3}$ alkyl)amino, phenylamino, naphthylamino, heteroaryl or heterocyclic amino wherein the heteroaryl or heterocyclic moiety is as hereinabove described in this paragraph, $NH_2C(O)$, mono- or di-($C_{1-3}$ alkyl) aminocarbonyl, $C_{1-4}$ alkyl-OC(O), $C_{1-5}$ alkyl-C(O)-$C_{1-4}$ alkyl, amino-$C_{1-5}$ alkyl and mono- or di-($C_{1-3}$) alkylamino-$C_{1-5}$ alkyl;

cyclopropanyl, cyclobutanyl, cyclopentanyl, cyclohexanyl, cycloheptanyl, bicyclopentanyl, bicyclohexanyl and bicycloheptanyl, each being optionally partially or fully halogenated and optionally substituted with one to three $C_{1-3}$ alkyl groups;

cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups; and $C_{1-6}$ alkyl branched or unbranched and optionally partially or fully halogenated;

$R_{11}$ is chosen from hydrogen and $C_{1-4}$ branched or unbranched alkyl which may optionally be partially or fully halogenated;

each $R_7$, $R_8$, $R_9$, $R_{10}$, is independently chosen from:
morpholine, piperidine, piperazine, imidazole and tetrazole;

wherein said method comprises:

reacting a compound of the formula (II) with a compound of the formula (III) under acid pH conditions, in a polar protic solvent under reflux for 5–16 hours, according to the scheme below:

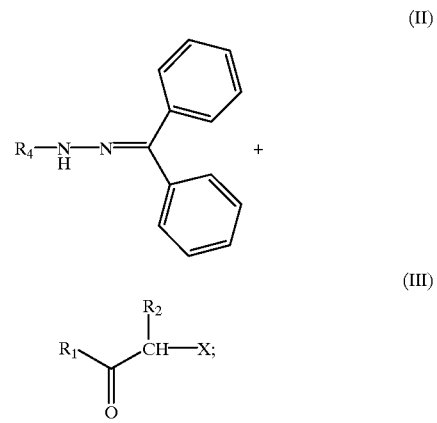

wherein X is chosen from —CN and —C(O)—$R_3$, wherein if X is CN then $R_3$ in the product formula (I) is amino;

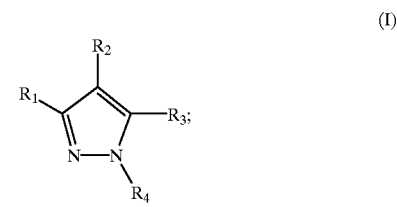

to form the product compound of the formula (I):
and subsequently isolating said product.

In another embodiment of the invention there is provided a process as described above and wherein $R_2$ is H;

In another embodiment of the invention there is provided a process as described immediately above and wherein:
the acid is chosen from HCl, AcOH, TFA and p-TsOH;
the solvent is a $C_1$–$C_3$ alcohol;
$R_1$ and $R_3$ are chosen from
amine, $C_{1-10}$ alkyl, alkoxy, phenyl, naphthyl, pyridinyl, pyrimidinyl, pyrazinyl, pyridazinyl, pyrrolyl, imidazolyl, pyrazolyl, thienyl, furyl, isoxazolyl and isothiazolyl; each of the aforementioned being optionally substituted with one to three groups chosen from halogen, $C_{1-6}$ alkyl and $C_{1-3}$ alkoxy; wherein when either $R_1$ or $R_3$ is amine the other is not amine; and $R_4$ is chosen from:

phenyl, naphthyl, pyridinyl, pyrimidinyl, pyrazinyl, pyrrolyl, imidazolyl and pyrazolyl, each of the aforementioned is optionally substituted with $C_{1-8}$ alkyl or $C_{1-6}$ branched or unbranched alkoxy each of which is optionally partially or fully halogenated.

In yet another embodiment, there is the process as described immediately above, and wherein the acid is chosen from HCl and p-TsOH; the solvent is ethanol, the reflux time is 5–8 hours, $R_3$ is amino and X is CN.

All terms as used herein in this specification, unless otherwise stated, shall be understood in their ordinary meaning as known in the art and be understood to be optionally substituted. For example, "alkoxy" is a alkyl with a terminal oxygen, such as methoxy, ethoxy and propoxy. All alkyl, alkenyl and alkynyl groups shall be understood as being branched or unbranched where structurally possible and unless otherwise specified. Other more specific definitions are as follows:

The term "aroyl" as used in the present specification shall be understood to mean "benzoyl" or "naphthoyl".

The term "heterocycle" refers to a stable nonaromatic 4–8 membered (but preferably, 5 or 6 membered) monocyclic or nonaromatic 8–11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Examples of heterocycles include but are not limited to, oxetanyl, pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl and dithianyl.

The term "heteroaryl" shall be understood to mean an aromatic 5–8 membered monocyclic or 8–11 membered bicyclic ring containing 1–4 heteroatoms such as N, O and S. Examples of such heteroaryls include: pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzooxazolonyl, benzo[1,4]oxazin-3-onyl, benzodioxolyl, benzo[1,3]dioxol-2-onyl, tetrahydrobenzopyranyl, indolyl, indolinyl, indolonyl, indolinonyl and phthalimidyl.

The term "aryl" as used herein shall be understood to mean phenyl, tolyl or naphthyl.

Terms which are analogs of the above cyclic moieties such as aryloxy or heteroaryl amine shall be understood to mean an aryl, heteroaryl and heterocycle as defined above attached to it's respective functional group.

As used herein, "nitrogen" and "sulfur" include any oxidized form of nitrogen and sulfur and the quaternized form of any basic nitrogen.

The term "halogen" as used in the present specification shall be understood to mean bromine, chlorine, fluorine or iodine.

ETOH shall be understood to mean ethanol.

p-TsOH is para-toluenesulphonic acid.

TFA is trifluoroacetic acid.

AcOH is acetic acid.

DPPF is diphenylphosphinoferocene.

The method of the invention is directed to only making compounds which are contemplated to be 'chemically stable' as will be appreciated by those skilled in the art. For example, a compound which would have a 'dangling valency', or a 'carbanion' are not compounds contemplated by the invention.

The general reaction scheme describing this invention is illustrated below. A benzophenone hydrazone of formula (II) is reacted with a 1,3-bifunctional intermediate of formula (III) under acid pH conditions, in a polar protic solvent for about 5–16 hours, where X is a carbonyl bearing $R_3$ (—C(O)$R_3$), or a nitrile (—CN), in which case $R_3$ will be an amine (NH$_2$) in the product of formula (I). Regarding preferred reaction time, 5–8 hours is preferred where X is —C(O)$R_3$ and 8–16 hours where X is CN. $R_1$, $R_2$, $R_3$, $R_4$ and X are as defined hereinabove:

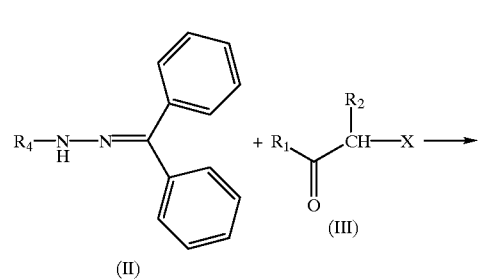

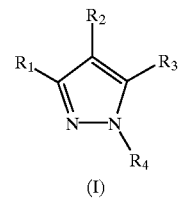

In one embodiment of the invention, the different acidic conditions can be obtained with acids chosen from: HCl, AcOH, TFA and p-TsOH. In yet another embodiment desirable yields are obtained by using p-TsOH or HCl in ethanol.

Schemes 1, 2, 3 and 4 represent specific aspects of the invention. These schemes are illustrative and, as recognized by one skilled in the art, particular reagents or conditions could be modified as needed for individual compounds without undue experimentation. Starting materials used in the schemes below are either commercially available or easily prepared from commercially available materials by those skilled in the art. Isolation and purification methods for particular compounds will be apparent to those of ordinary skill, a non-limiting example of which is provided in Example 1 below.

Aryl hydrazones 3, 4 and 11 were prepared by Pd-catalyzed cross-coupling of the corresponding aryl bromide with benzophenone hydrazone, following the recently reported procedure by Hartwig.[3b] The hydrazones were obtained in 85–99% yields. See Scheme 1 below.

Scheme 1

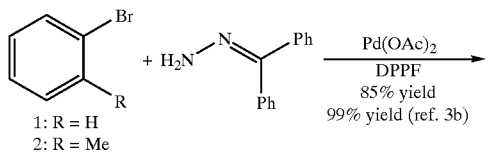
1: R = H
2: R = Me

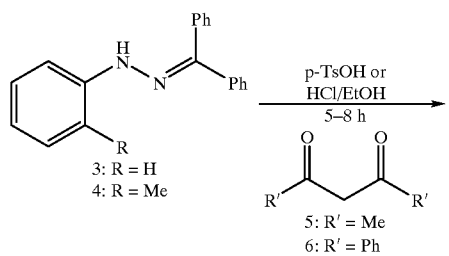
3: R = H
4: R = Me
5: R′ = Me
6: R′ = Ph

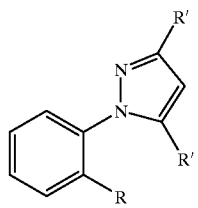
7: R = H, R′ = Ph; 88%
8: R = Me, R′ = Ph; 94%
9: R = R′ = Me; 84%

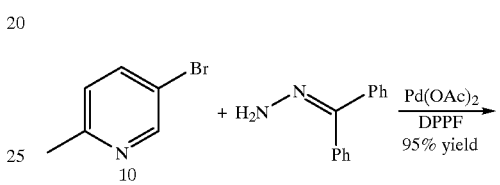
10

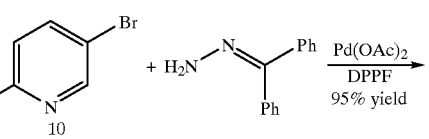
11

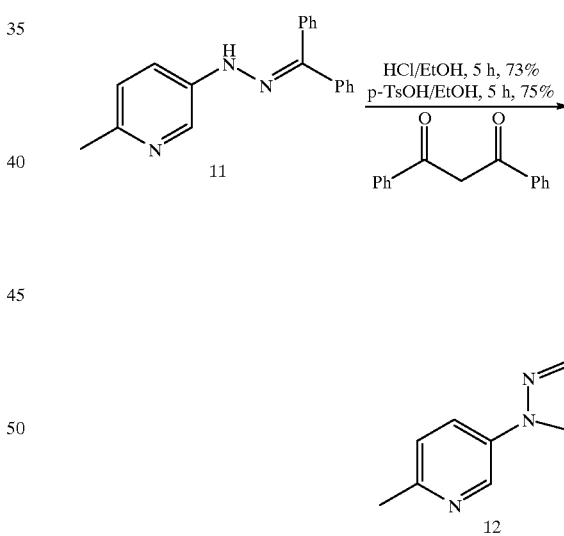
12

The synthesis of pyrazoles is accomplished by refluxing hydrazones 3, 4 and 11 (shown below) with symmetrical 1,3-diketones 5 and 6 in ethanol under acidic conditions. Pyrazoles 8, 9 and 12 were prepared in 75–94% isolated yields using p-TsOH. Similar yields were obtained in preparing pyrazoles 7 and 12 under HCl/EtOH conditions.[5]

The results with symmetrical diketones prompted examination of the regioselective synthesis of unsymmetrical pyrazoles or pyrazole-related structures from aryl hydrazones 3 and 4. As illustrated in Scheme 2 treatment of 3 with ethyl acetoacetate, under p-TsOH/EtOH conditions, has provided pyrazoles 14 and pyrazolone 15 in 3:1 ratio respectively and 52% isolated yield. See Example 1. Interestingly, replacing p-TsOH with HCl provided 14a and 15a in 1:1 ratio and 58% yield. The stability of 14a and 15a under the p-TsOH and HCl reaction conditions was examined and no interconversion was detected in both compounds. On the other hand, a single product (14b) was formed in 41% yield upon treatment of 4 with p-TsOH and a 4:1 ratio of 14b:15b was obtained in 38% yield under the HCl conditions.

Synthesis of pyrazolones 17 was accomplished by treatment of 3 or 4 with ethyl malonyl chloride in refluxing dioxane, affording after 10 min the corresponding compound 16 in 80–83% isolated yield. Subsequent cyclization of 16 in p-TsOH/EtOH afforded, after 1.5 h, pyrazolones 17 in 68–70% yield. The $^1$H-NMR of compound 17a is in full agreement with previously reported data.[5]

Scheme 3

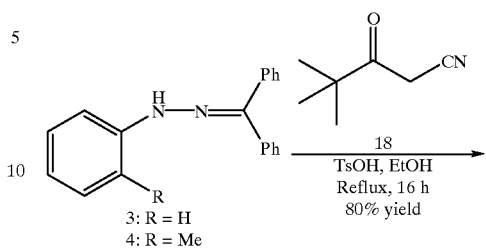

Scheme 2

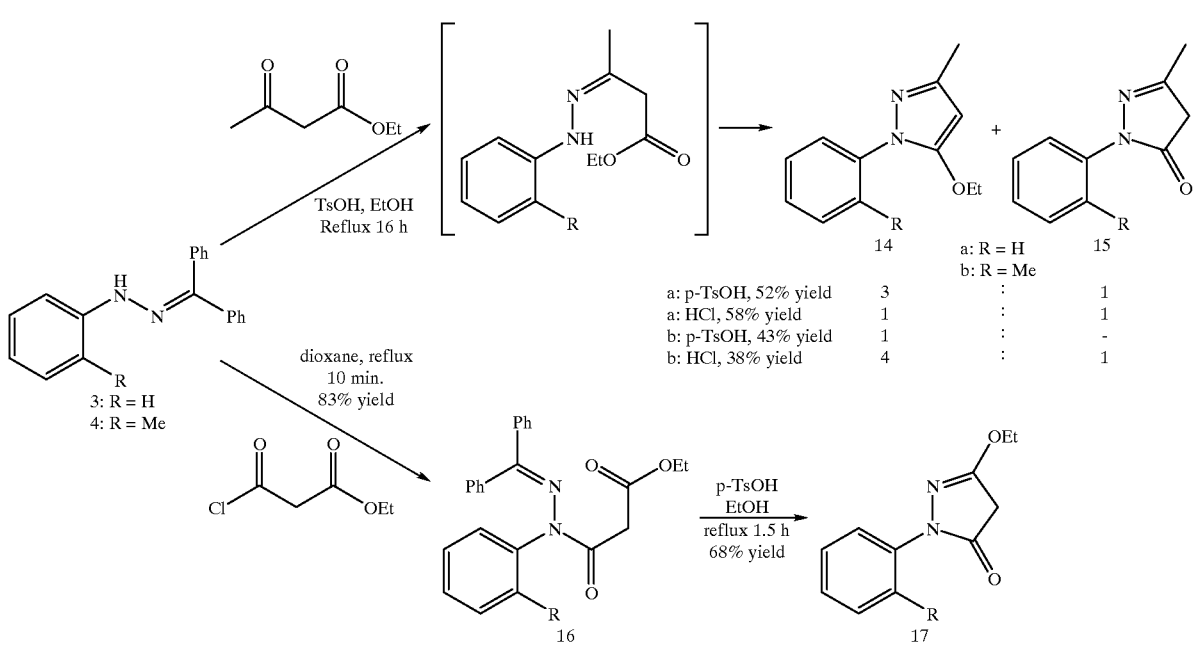

Preparation of pyrazole amines was expected to be possible by treating hydrazones with cyanoketone 18 under acidic conditions as illustrated in Scheme 3. Similar selectivity in the transhydrazonation to that obtained with β-ketoesters should provide pyrazole amines of type 19. Treatment of aryl hydrazones 3 and 4 with 18 afforded single products 19 and 20 respectively in 80% isolated yields. The structure of 19 was confirmed by its preparation from hydrazine 21 with cyanoketone 18 under similar reaction conditions. The utility of the cross coupling-pyrazole formation sequence was further demonstrated in the synthesis of heteroaryl pyrazole 22 in 61% yield.

-continued

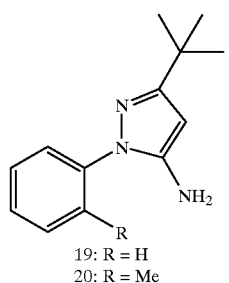

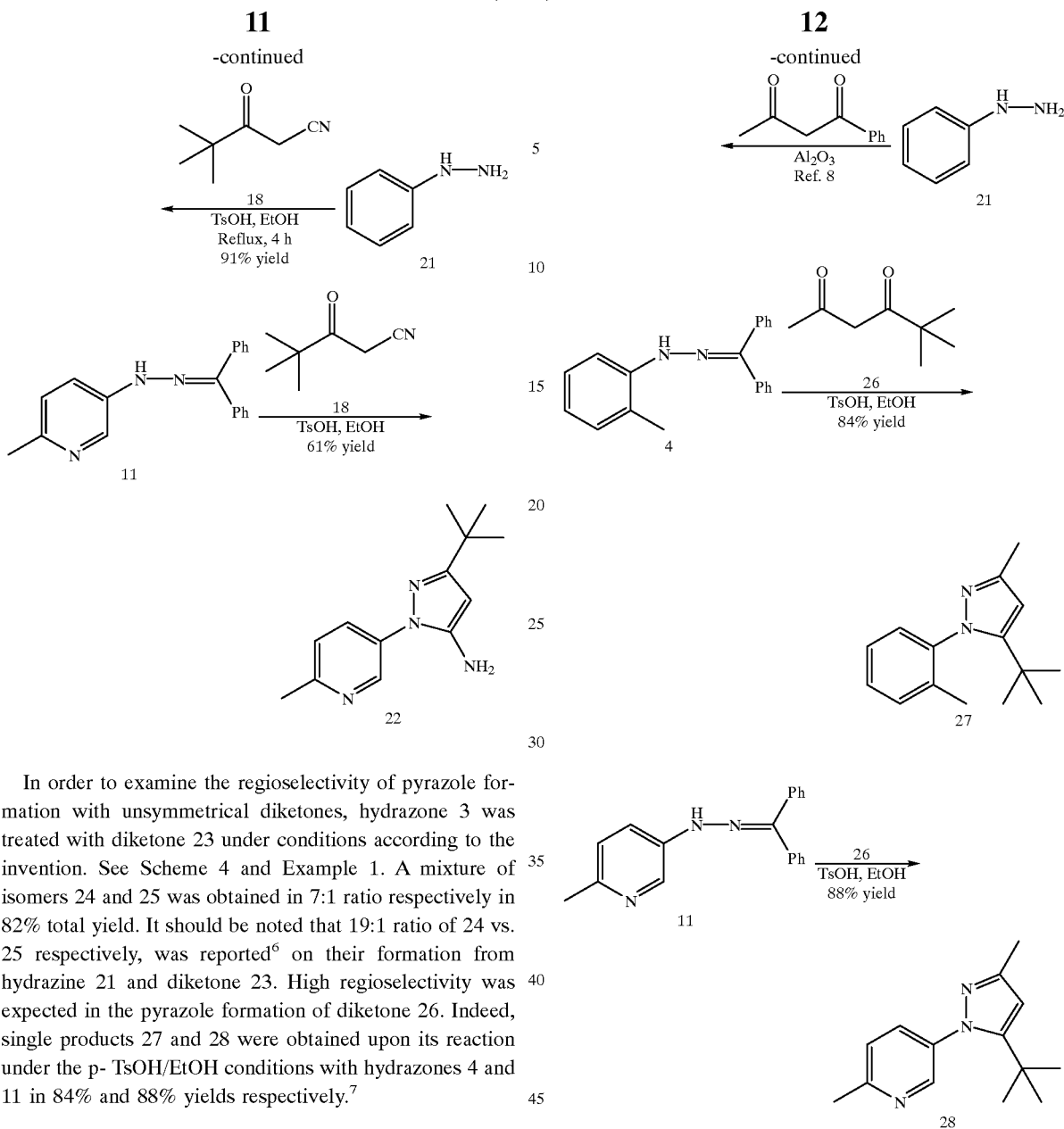

In order to examine the regioselectivity of pyrazole formation with unsymmetrical diketones, hydrazone 3 was treated with diketone 23 under conditions according to the invention. See Scheme 4 and Example 1. A mixture of isomers 24 and 25 was obtained in 7:1 ratio respectively in 82% total yield. It should be noted that 19:1 ratio of 24 vs. 25 respectively, was reported[6] on their formation from hydrazine 21 and diketone 23. High regioselectivity was expected in the pyrazole formation of diketone 26. Indeed, single products 27 and 28 were obtained upon its reaction under the p-TsOH/EtOH conditions with hydrazones 4 and 11 in 84% and 88% yields respectively.[7]

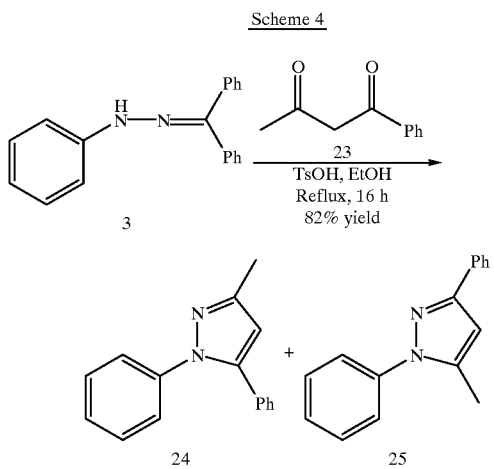

In order that this invention be more fully understood, the following examples 1(a) and (b) are set forth. These examples are for the purpose of illustrating embodiments of this invention, and are not to be construed as limiting the scope of the invention in any way.

EXAMPLE 1

1(a) with p-TsOH/EtOH:

A solution of the benzophenone hydrazone (1.75 mmol), p-TsOH (1.0 g) and the bi-functional substrate (2.63 mmol) in EtOH (10 mL) was refluxed for a period of 8–16 h. The reaction mixture was cooled to RT, then NaHCO$_3$ saturated solution (10 mL) and EtOAc (10 mL) were added. The layers were separated, and the aqueous layer washed with EtOAc. The combined organics dried (Na$_2$SO$_4$), concentrated then purified by column chromatography.

1(b) with HCl/EtOH:

The reactions were carried out in a saturated solution of HCl in EtOH with a similar ratio of reactants and concentration as described in (a). Excess saturated NaHCO$_3$ was added to ensure complete neutralization of the HCl.

All new compounds were characterized by full spectroscopic data, yields refer to chromatographed materials with purity of >95%. Selected $^1$H-NMR data from 14a: δ 5.47 (1H, s), 4.12 (2H, q), 2.28 (3H, s), 1.43 (3H, t); 14a (literature[a]): δ 5.50 (1H, s), 4.14 (2H, q), 2.26 (3H, s), 1.41 (3H, t); 14b: δ 5.44 (1H, s), 4.07 (2H, q), 2.26 (3H, s), 1.33 (3H, t). (a) Katritzky, A. R.; Main, F. W. *Tetrahedron* 1964, 20, 299; $^1$H-NMR of 15a found in full agreement with reported data: DeRuiter, J.; Carter, D. A.; Arledge, W. S.; Sullivan, P. J. *J. Heterocyclic Chem.* 1987, 24, 149.

TABLE 1

The following compounds were prepared using methods similar to Examples 1(a) and (b).

| R$_1$ | R$_2$ | R$_3$ | R$_4$ |
|---|---|---|---|
| Phenyl | H | NH$_2$ | 2-methylphenyl |
| methyl | H | methyl | 2-methylphenyl |
| methyl | Methyl | methyl | 2-methylphenyl |
| methyl | Benzyl | methyl | 2-methylphenyl |
| methyl | Phenyl | NH$_2$ | 2-methylphenyl |

REFERENCES AND NOTES 1. (a) Makino, K.; Kim, H. S.; Kurasawa, Y. *J Heterocyclic Chem.* 1998, 35, 489; (b) Elguero, *J. Compr. Heterocycl. Chem.* II 1996, 3, 1.
2. For reviews on the synthesis of pyrazoles and pyrazole related structures see: ref. 1 and (a) Takagi, K.; Huber-Habart, M. *J. Heterocyclic Chem.* 1996, 33, 1003; (b) El-Rayyes, N. R.; Al-Awadi, N. A. *Synthesis* 1985, 1028; (c) Sammes, M. P.; Katritzky, A. R. *Advances in Heterocyclic Chemistry*, Vol 34, Academic Press, 1983; (d) Behr, L. C.; Fusco, R.; Jarboe, C. H. *The Chemistry of Heterocyclic Compounds*, Weissberger, A., ed., Interscience Publishers, John Wiley and Sons, 1967.
3. (a) Wagaw, S.; Yang, H. B.; Buchwald, S. L. *J. Am. Chem. Soc.* 1998, 120, 6621; (b) Hartwig, J. F. *Angew. Chem., Int. Ed.* 1998, 37, 2090.
4. For palladium catalyzed coupling of t-butylcarbazate with activated aryl bromides see: Wang, Z.; Skerlj, R. T.; Bridger, G. J. *Tet. Lett.* 1999, 40, 3543.
5. Selected $^1$H-NMR data from 17a: δ 4.35 (2H, q), 3.48 (1H, s); 17a(literature[7a]): δ 4.34 (2H, q), 3.47 (1H, s); 17b: δ 4.27 (2H, q), 3.46 (1H, s); (a) Molinari, A.; Oliva, A. *J. Heterocyclic Chem.* 1996, 33, 479.
6. Texier-Boullet, F.; Klein, B.; Hamelin, J. *Synthesis* 1986, 409.
7. The regioselectivity in structures 27 and 28 were confirmed by the NOE between the t-butyl with the N-aryl substituent, determined by NOESY.

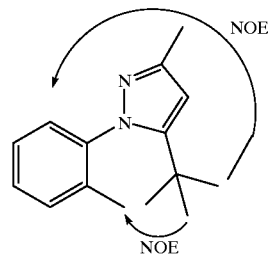

27

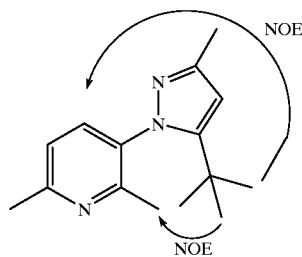

28

All references cited in this application are incorporated herein by reference in their entirety.

What is claimed is:

1. A method of making a pyrazole compound of the formula (I):

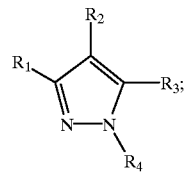

(I)

wherein R$_1$, R$_2$, R$_3$ and R$_4$ are defined as follows:
each R$_1$ and R$_3$ are independently chosen from: amino and C$_{1-10}$ alkyl optionally partially or fully halogenated and optionally substituted with one to three C$_{3-10}$ cycloalkanyl, C$_{1-6}$alkoxy, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl; each of the aforementioned being optionally substituted with one to five groups chosen from halogen, C$_{1-6}$ alkyl which is optionally partially or fully halogenated, C$_{3-8}$ cycloalkanyl, C$_{5-8}$ cycloalkenyl and C$_{1-3}$ alkoxy which is optionally partially or fully halogenated; wherein both R$_1$ and R$_3$ cannot simultaneously be amino;

R$_2$ is chosen from:
hydrogen, C$_{1-6}$ branched or unbranched alkyl optionally partially or fully halogenated and aryl optionally partially or fully halogenated;

R$_4$ is chosen from:
phenyl, naphthyl, pyridinyl, pyrimidinyl, pyrazinyl, quinolinyl and isoquinolinyl, each of the aforementioned is optionally substituted with one to three phenyl, naphthyl, heterocycle or heteroaryl as hereinabove described in this paragraph, C$_{1-6}$ branched or unbranched alkyl which is optionally partially or fully halogenated, cyclopropanyl, cyclobutanyl, cyclopentanyl, cyclohexanyl, cycloheptanyl, bicyclopentanyl, bicyclohexanyl, bicycloheptanyl, phenyl C_{1-5} alkyl, naphthyl C_{1-5} alkyl, halogen, hydroxy, oxo, nitrile, C_{1-3} alkoxy optionally partially or fully halogenated, phenyloxy, naphthyloxy, heteroaryloxy or heterocyclicoxy wherein the heterocyclic or heteroaryl moiety is as hereinabove described in this paragraph, nitro, phenylamino, naphthylamino, heteroaryl or heterocyclic amino wherein the heteroaryl or heterocyclic moiety is as hereinabove described in this paragraph, NH_2C(O), a mono- or di-(C_{1-3}alkyl) aminocarbonyl, C_{1-5} alkyl-C(O)—C_{1-4} alkyl, amino-C_{1-5} alkyl, mono- or di-(C_{1-3} alkyl) amino-C_{1-5} alkyl, amino-S(O)_2, di-(C_{1-3}alkyl)amino-S(O)_2, R_7—C_{1-5} alkyl, R_8—C_{1-5} alkoxy, R_9—C(O)—C_{1-5} alkyl, R_{10}—C_{1-5} alkyl (R_{11})N or carboxy-mono-or di-(C_{1-5} alkyl)-amino;

R_{11} is chosen from hydrogen and C_{1-4} branched or unbranched alkyl which may optionally be partially or fully halogenated;

each R_7, R_8, R_9, R_{10}, is independently chosen from: morpholine, piperidine, piperazine, imidazole and tetrazole;

wherein said method comprises:

reacting a compound of the formula (II) with a compound of the formula (III) under acid pH conditions, in a polar protic solvent under reflux for 5–16 hours, according to the scheme below:

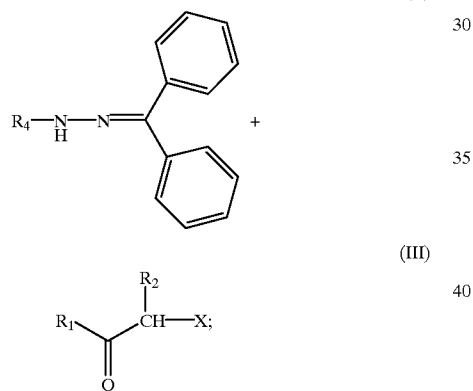

wherein X is chosen from —CN and —C(O)—R_3, wherein if X is CN then R_3 in the product formula (I) is amino;

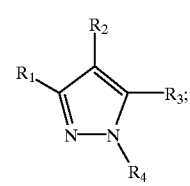

to form the product compound of the formula (I): and subsequently isolating said product.

2. The process according to claim 1, wherein R_2 is hydrogen.

3. The process according to claim 2, wherein the acid is chosen from HCl, AcOH, TFA and p-TsOH;

the solvent is a C_1–C_3 alcohol;

R_1 and R_3 are chosen from
  amino, C_{1-10} alkyl, alkoxy, phenyl, naphthyl, pyridinyl, pyrimidinyl, pyrazinyl, pyridazinyl, pyrrolyl, imidazolyl, pyrazolyl, thienyl, furyl, isoxazolyl and isothiazolyl; each of the aforementioned being optionally substituted with one to three groups chosen from halogen, C_{1-6}alkyl and C_{1-3} alkoxy; wherein when either R_1 or R_3 is amine the other is not amino; and R_4 is chosen from:
  phenyl, naphthyl, pyridinyl, pyrimidinyl and pyrazinyl, each of the aforementioned is optionally substituted with C_{1-6} branched or unbranched alkyl or C_{1-3} alkoxy each of which is optionally partially or fully halogenated.

4. The process according to claim 3 wherein:

the acid is chosen from HCl and p-TsOH;

the solvent is ethanol, the reflux time is 5–8 hours;

R_3 is amino and

X is CN.

* * * * *